United States Patent [19]

Vogelstein

[11] Patent Number: 5,580,729

[45] Date of Patent: *Dec. 3, 1996

[54] GENERALIZED METHOD FOR CANCER ASSESSMENT

[75] Inventor: Bert Vogelstein, Baltimore, Md.

[73] Assignee: The Johns Hopkins University, Baltimore, Md.

[ * ] Notice: The portion of the term of this patent subsequent to Jan. 10, 2012, has been disclaimed.

[21] Appl. No.: 264,934

[22] Filed: Jun. 24, 1994

Related U.S. Application Data

[63] Continuation of Ser. No. 324,512, Mar. 16, 1989, Pat. No. 5,380,645.

[51] Int. Cl.$^6$ .............................. C12Q 1/68; C12P 19/34; C07H 21/04; C12N 15/00

[52] U.S. Cl. ........................... 435/6; 435/91.1; 435/91.2; 435/810; 536/23.5; 536/24.33; 536/25.3; 935/8; 935/76; 935/77; 935/78

[58] Field of Search ............................. 435/6, 91.1, 91.2, 435/810; 536/23.1, 23.5, 24.33, 25.3, 25.4; 935/8, 76–78

[56] References Cited

U.S. PATENT DOCUMENTS

| | | |
|---|---|---|
| 4,683,202 | 7/1987 | Mullis . |
| 5,098,823 | 3/1992 | Bodmer et al. . |
| 5,380,645 | 1/1995 | Vogelstein .................................. 435/6 |

OTHER PUBLICATIONS

Reichmann et al., "Chromosomal Banding Patterns in Human Large Bowel Cancer", *Int. J. Cancer* 28:431–440 (2981).
Wolley et al., "DNA Distribution in Human Colon Carcinomas and its Relationship to Clinical Behavior", *Journal of the National Cancer Inst.*, 69:15–22 (1982).
Barlogie et al., "Flow Cytometry in Clinical Cancer Research", *Cancer Research*, 43:3982–3997 (1983).
Fearon et al., "Loss of Genes on the Short Arm of Chromosome 11 in Bladder Cancer", *Nature*, 318:377–380 (1985).
Goelz et al., "Purification of DNA from Formaldehyde Fixed and Paraffin Embedded Human Tissue", *Biochem and Biophys. Res. Comm.*, 130:118–126 (1985).
Jeffreys et al., "Hypervariable 'Minisatellite' Regions in Human DNA", *Nature*, 314:67–73 (1985).
Muleris et al., "Consistent Deficiencies of Chromosome 18 and of the Short Arm of Chromosome 17 in Eleven Cases of Human Large Bowel Cancer: A Possible Recessive Determinism", *Ann. Gent.*, 28:206–213 (1985).
Melamed et al., "Flow Cytometry Off Colorectal Carcinoma with Three–Year Follow–up", *Dis. Colon Rectum* 29:184–186 (1986).

Ali et al., "Reduction to Homozygosity of Genes on Chromosome 11 in Human Breast Neoplasia", *Science* 238:185–188 (1987).
Fearon et al., "Clonal Analysis of Human Colorectal Tumors", *Science* 238:193–197 (1987).
Nakamura et al., "Variable Number of Tandem Repeat (VNTR) Markers for Human Gene Mapping", *Science* 235:1616–1622 (1987).
Quirke et al. "Prognostic Significance of DNA Aneuploidy and Cell Proliferation in Rectal Adenocarcinomas", *J. Pathology* 151:285–291 (1987).
Solomon et al., "Chromosome 5 Allele Loss in Human Colorectal Carcinomas", *Nature* 328:616–619 (1987).
Law et al., "Concerted Nonsystemic Allelic Loss in Human Colorectal Carcinoma," *Science* 241:961–964 (1988).
Monzepat et al., "Loss of Alleles on Chromosome 18 and on the Short Arm of Chromosome 17 in Polyploid Colorectal Carcinomas," *Int. J. Cancer* 41:404–408 (1988).
Okamoto et al., "Loss of Constitutional Heterozygosity in Colon Carcinoma from Patients with Familial Polyposis Coli," *Nature* 331:273–277 (1988).
Vogelstein et al., "Genetic Alterations During Colorectal–Tumor Development", *New England Jour. of Med.* 319:525–532 (1988).
Krontiris et al., "Human Restriction Fragment Length Polymorphisms and Cancer Risk Assessment," *J. Cellular Biochemistry* 30:319–329 (1986).
Khosla et al., *J. Clin. Invest.* 887:1691 (1991).
Yamaguchi et al. "Allelotype Analysis in Osteosarcomas: Frequent Allele Loss on 3q, 13q, 17p, and 18q", *Cancer Research* 52:2419–2423 (1992).
Tsuchiya et al., "Allelotype of Non–Small Cell Lung Carcinoma–Comparison Between Loss of Heterozygosity in Squamous Cell Carcinoma and Adenocarcinoma", *Cancer Research* 52:2478–2481 (1992).
Sato et al., "Allelotype of Breast Cancer: Cumulative Allele Losses Promote Tumor Progression in Primary Breast Cancer", *Cancer Research* 50:7184–7189 (1990).
Sato et al., "Allelotype of Human Ovarian Cancer", *Cancer Research* 51:5118–5122 (1991).
Sato et al., "Accumulation of Genetic Alterations and Progression of Primary Breast Cancer", *Cancer Research* 51:5794–51222 (1991).

(List continued on next page.)

*Primary Examiner*—W. Gary Jones
*Assistant Examiner*—Bradley L. Sisson
*Attorney, Agent, or Firm*—Banner & Allegretti, Ltd.

[57] ABSTRACT

A method is provided for assessing the generalized genetic change which occurs during tumorigenesis. The method relies on measurement of loss of a large number of alleles from the chromosomes of the tumor cells. The alleles are RFLP markers. The role of any of the particular alleles in tumorigenesis need not be known. The amount of allelic loss allows a prognosis to be made regarding tumor metastasis, tumor recurrence, and mortality.

25 Claims, 4 Drawing Sheets

OTHER PUBLICATIONS

Morita et al., "Allelotype of Renal Cell Carcinoma", *Cancer Research* 51:820–823 (1991).

Kunimi et al., "Allelotyping of Human Prostatic Adenocarcinoma", *Genomics* 11:530–536 (1991).

Sano et al., "Frequent Loss of Heterozygosity on Chromosomes 1q, 5q, and 17p in Human Gastric Carcinomas", *Cancer Research* 51:2926–2931 (1991).

Fujimori et al., "Allelotype Study of Primary Hepatocellular Carcinoma", *Cancer Research* 51:89–93 (1991).

Vogelstein et al., "Allelotype of Colorectal Carcinomas", *Science* 244:207–211 (1989).

Morita et al., "Common Regions of Deletion on Chromosomes 5q, 6q, and 10q in Renal Cell Carcinoma", *Cancer Research* 51:5817–5820 (1991).

Mulder et al., "The Relationship of Quantitative Nuclear Morphology to Molecular Genetic Alterations in the Adenoma–Carcinoma Sequence of the Large–Bowel", *American Journal of Pathology*, V141, N4 (1992) Abstract.

Fong et al., "Loss of Heterozygosity for Chromosome–1 or Chromosome–14 Defines Subsets of Advanced Neuroblastomas", *Cancer Research*, V52, N7 (1992).

Goyette et al., "Progression of Colorectal Cancer is Associated with Multiple Tumor Suppressor Gene Defects But Inhibition of Tumorigenicity is Accomplished by correction of any single Defect Via Chromosome Transfer", *Molecular Cell Biology* 12(3):1387–1395 (1992).

Kern et al., "Clinical and Pathological Associations with Allelic Loss in Colorectal Carcinoma", *JAMA* 21:3099–3103 (1989).

Johan Offerhaus et al., "The Relationship of DNA Aneuploidy to Molecular Genetic Alterations in Colorectal Carcinoma" *Gastroenterology* 102(5):1612–1619 (1992).

Milliken et al., "Loss of Heterozygosity for Loci on the Long Arm of Chromosome 6 in Human Malignant Melanoma", *Cancer Research* 51(20):5449–5453 (1991).

Miyoshi et al., "Insertion–Deletion Polymorphisms and Other Restriction Fragment Length Polymorphisms in the MCC Gene", *Japanese Journal of Cancer Research*, 83(1):10–14 (1992).

Sidransky et al., "Clonal Origin of Bladder Cancer", *New Engl. J. Medicine* 326(11):737–740 (1992).

Niermon et al., eds., *ATCC NIH Repository of Human DNA Probes and Libraries*, 1988.

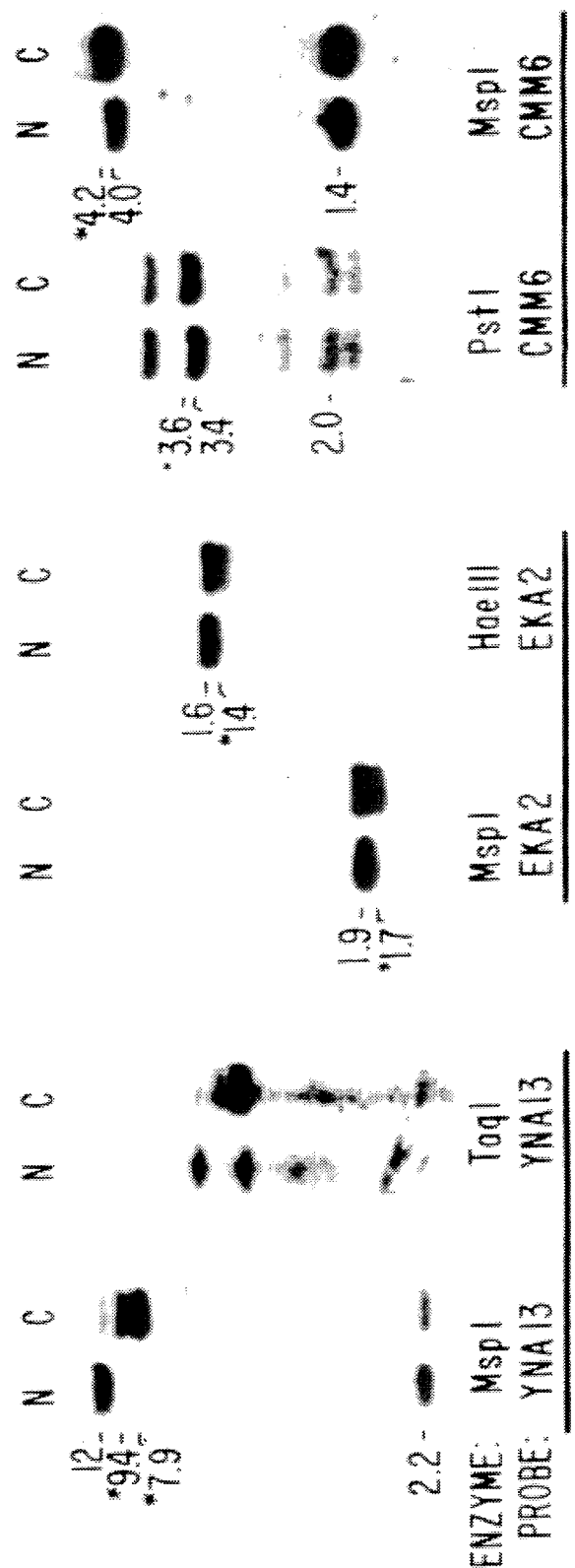

GENERALIZED METHOD FOR CANCER ASSESSMENT

The U.S. Government has a paid-up license in this invention and the right in limited circumstances to require the patent owner to license others on reasonable terms as provided for by the terms of grants GM07309 and GM07184 and CA41183, CA47527 and CA35494 from the National Institutes of Health.

This application is a continuation of application Ser. No. 07/324,512, filed Mar. 16, 1989 which issued as U.S. Pat. No. 5,380,645 on Jan. 10, 1995.

BACKGROUND OF THE INVENTION

Previous reports have focused on the loss of particular alleles in particular cancers. For example, deletions of chromosomal arm 13q are associated with retinoblastoma. (Cavenee et al., Nature, Vol. 305, p. 779 (1983).) In such cases, the deletions are thought to involve tumor suppressor genes, which while present in the genome, suppress unregulated growth.

In contrast with such examples of particular genes associated with particular cancers, more general studies using techniques such as flow cytometry and karyotypic analysis have indicated that gross chromosomal abnormalities occur in cancer cells. These include deletions, translocations, and duplications. However, up until now no method has been provided in the art which assesses overall chromosomal abnormalities at the molecular level. There is a need in the art for such a method and for molecular means of providing prognoses of tumor recurrence, tumor metastasis, and mortality.

SUMMARY OF THE INVENTION

It is an object of the invention to provide a method of assessing the extent of genetic change in neoplastic tissue.

It is another object of the invention to provide a method of assessing the extent of genetic change in neoplastic tissue which relies neither on karyotypic analysis nor on analysis of particular genes implicated in carcinogenesis.

It is yet another object of the present invention to provide a method of assessing the extent of genetic change in neoplastic tissue in which the loss of a set of polymorphic alleles is measured.

It is still another object of the present invention to provide a method of assessing the genetic change in neoplastic tissue so that a prognosis of a patient can be determined.

It is another object of the invention to provide a kit for assessing the extent of genetic change in neoplastic tissue.

These and other objects of the invention are provided by one or more of the embodiments described below. The present invention provides a method of assessing the extent of genetic change in neoplastic tissues, comprising the steps of:

isolating a first sample of DNA from a neoplastic tissue of a patient and a second sample of DNA from a non-neoplastic tissue of the patient;

testing the first and second DNA samples for the presence of a set of alleles;

determining a percentage of loss in the first sample relative to the second sample of alleles in said set for which the patient is heterozygous, wherein said set has a sufficient number of alleles such that the percentage of loss of alleles of said set for which the patient is heterozygous provides a measure of genetic change in the tumor tissue correlating with prognosis.

In another embodiment of the invention the presence of a set of alleles is tested by performing Southern hybridization of the DNAs of the first and second samples with a set of nucleic acid probes which detect restriction fragment length polymorphisms.

In yet another embodiment of the invention, the presence of a set of alleles in said first and second DNA samples is tested by amplification of regions of the DNA of said first and second samples using pairs of primers which bracket regions of DNA containing restriction fragment length polymorphisms.

In a preferred embodiment of the present invention, the set of alleles which are tested for loss comprise at least one allele from each of the non-acrocentric chromosomal arms of the human genome.

In still another embodiment of the invention a kit is provided comprising a set of nucleic acid probes for human alleles, said set detecting a sufficient number of alleles such that the cumulative loss in neoplastic tissue of alleles detected by said set of probes for which the patient is heterozygous provides a measure of the extent of genetic change in the neoplastic tissue, the extent of genetic change being correlated with prognosis, said probes detecting restriction fragment length polymorphisms.

In another embodiment of the invention a kit is provided which comprises a set of single-stranded nucleic acid primer pairs for human DNA. A pair of primers brackets a region containing a restriction fragment length polymorphism. The set of primer pairs contain a sufficient number of primer pairs such that the cumulative loss in a neoplastic tissue of a patient of restriction fragment length polymorphism alleles bracketed by said set of primer pairs for which the patient is-heterozygous provides a measure of genetic change which correlates with prognosis.

The present invention provides the art with a generalized method which can be applied to all types of neoplastic tissues which can be isolated apart from normal, non-neoplastic tissues, to provide a prognostic indicator of the course of the neoplasm. The method does not rely on any particular genetic change occurring in any particular disease.

BRIEF DESCRIPTION OF THE DRAWINGS

FIG. 3 shows an example of allelotypic analysis comparing DNA from normal (N) and carcinoma (C) tissues. FIGS. 3A, 3B, 3C, 3D, 3E and 3F represent six different patients, S141, S7, S191, S153, S98, and S175, respectively. The restriction enzyme and radioactive probe used are listed below each blot.

DETAILED DESCRIPTION OF THE INVENTION

Figure 1:
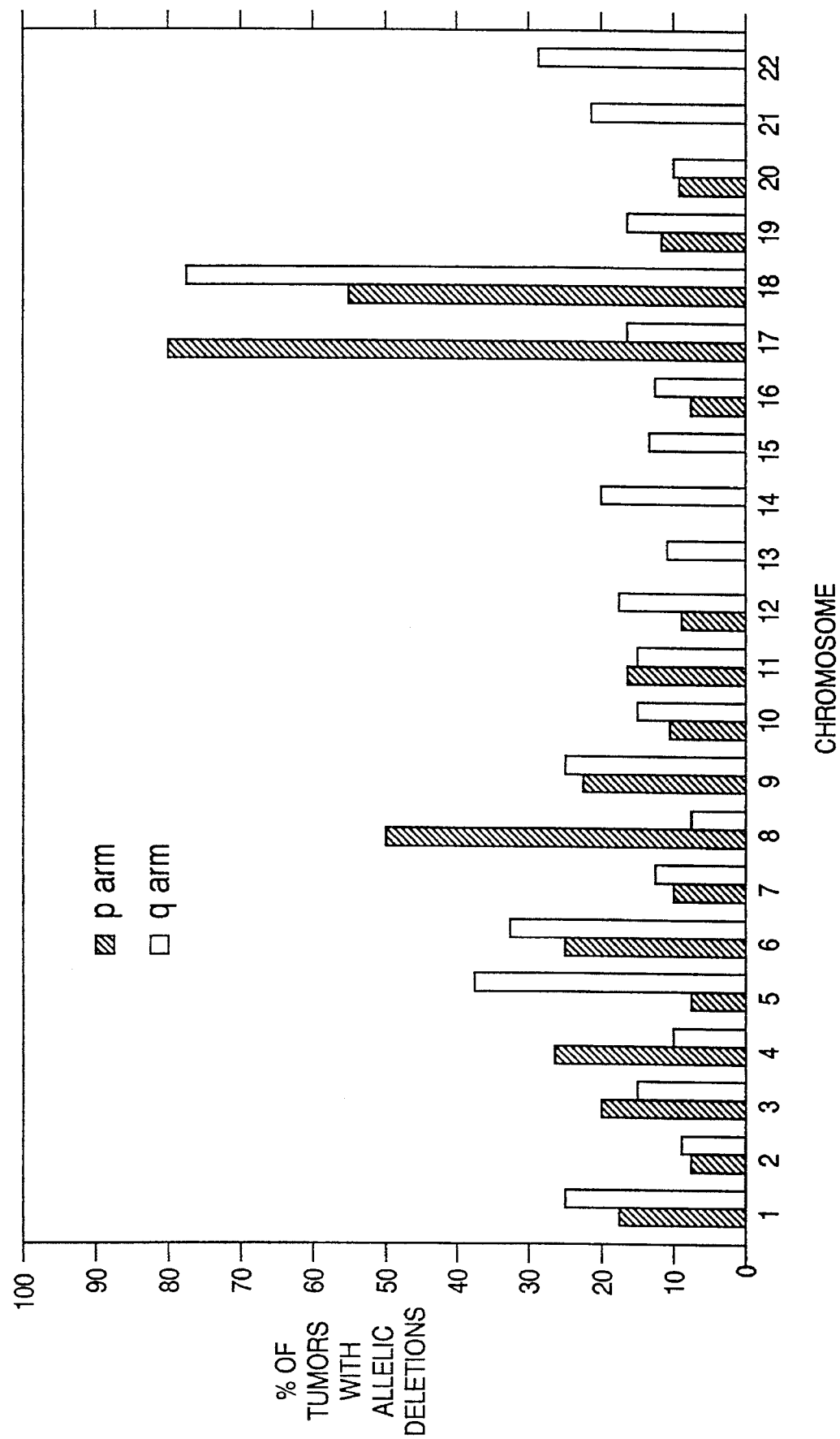
FIG. 1 shows graphically the frequency of allelic deletions in individual chromosomal arms as detected by the analysis.

It is a finding of the present invention that allelic loss in tumor cells is remarkably common. One of the alleles of each polymorphic marker tested was found to be deleted in at least some tumors. Some tumors lost more than half of their parental alleles. Furthermore, it has been found that the amount of allelic deletions in tumor tissue has prognostic value for the patient. Regardless of the size and stage of the primary tumor which a patient may have, the percentage of allelic deletions can provide a prediction of tumor recurrence and metastasis, as well as of resulting death. Thus, the determination of the status of allelic losses in a tumor, called a tumor allelotype, provides a molecular measure for prognosis in patients with cancers.

Although less frequent than deletions, new DNA fragments were found in some tumor tissues which were not present in the corresponding normal tissue. The new fragments contained repeated sequences of the VNTR type (variable number of tandem repeats).

The extent of genetic change which is measured by the method of the present invention is a nonspecific measurement which is independent of particular genes or loci. Thus a variety of different alleles may comprise the set for which the present method tests without altering the prognostic value of the test. However, a sufficient number of alleles must be used such that the cumulative (or percentage) loss of alleles provides a measure of the extent of genetic change in the neoplastic tissue which is correlated with prognosis. A preferred set of alleles comprises alleles on each of the non-acrocentric arms of the set of human chromosomes. (Acrocentric arms are thought to contain mainly the genes for ribosomal RNA which are repeated multiply in the genome. The repeated nature of these sequences would make it difficult to detect deletions of single copies.) Other sets or subsets of alleles may be used so long as they are still able to provide a measure of the extent of genetic change which correlates with prognosis such as that provided by the preferred set of alleles.

Each probe of the present invention defines a restriction fragment length polymorphism (RFLP). That is to say that if one were to screen a normal human population for the presence of such an allele, greater than 5% of the humans would display a different sized restriction fragment corresponding to the allele. A particular type of RFLP probe which can be used in the present invention are probes for a variable number of tandem repeats (VNTR).

In order to detect allelic loss in humans it is desirable that the allele being tested is present in two different forms in the normal tissue of the patient. Thus the patient would be heterozygous for the particular allele. This renders analysis of allelic deletion simple and reliable. In general, only a single copy of the two alleles which are present in a human are lost upon allelic deletion in tumorigenesis; the existence of two distinctly sized fragments for each allele renders the observation of loss of a single allele a qualitative rather than a quantitative measurement. That is to say, in order to score the loss of a heterozygous allele one looks for absence of a particular sized fragment. If in the normal tissue the patient were homozygous for the allele, upon loss of a single copy of that allele the restriction fragment containing the allele would decrease in intensity by about 50%. Total loss is much easier to detect than a 50% loss.

Nucleic acid probes which detect restriction fragment length polymorphisms for most non-acrocentric chromosome arms are available from the American Type Culture Collection, Rockville, Md. These are described in the NIH Repository of Human DNA Probes and Libraries, published in August, 1988.[1] Methods of obtaining other probes which detect restriction fragment length polymorphisms are known in the art. The statistical information provided by using the complete set of probes which hybridizes to each of the non-acrocentric arms of the human genome is useful prognostically. Other subsets of this complete set can be used which also will provide useful prognostic information. Other subsets can be tested to see if their use leads to measures of the extent of genetic change which correlates with prognosis, as does the use of the complete set of alleles.

[1] One probe called MCT112 hybridizes to the 9p chromosome arm, although it is listed in the catalog as hybridizing to 9q. Another probe, EFD75, which hybridizes to the 10q arm is listed as hybridizing to chromosome number 10. Probes for chromosome arm 8p are not listed in the NIH Repository, but are taught in two references: Lacoste-Royal et al., Nucleic Acid Res., Vol. 16, p. 4184 (1988); and Wood et al., Cytogenet. Cell Genet., Vol. 42, p. 113 (1986).

In the case of colorectal carcinomas the median amount of allelic deletions found in each tumor is about 20% of those alleles tested. It was found that patients with allelic loss higher than the median were at a significantly greater risk of tumor recurrence and death than those with allelic loss below the median. The suitability of other sets of alleles as a prognostic indicator should be tested on a population of colorectal cancer patients to be sure that similar amounts of allelic loss are found in the population, and that the amount of allelic loss can be correlated with tumor recurrence and death.

To find characteristic levels of allelic loss for other types of cancers, a population of patients having the same type of cancer should be evaluated. Preferably the population will have 50 or more patients in it. Although the median amount of allelic lass for a variety of types of cancers may vary from type to type, the same trend will hold for all. Larger amounts of allelic loss in a particular tumor indicates a higher risk of tumor recurrence and death, whereas lower amounts of allelic loss indicate a lower risk. Other tumor types for which the method of the invention is useful include carcinomas of the lung, colon, breast, bladder, prostate, liver, and stomach.

According to the method of the present invention, two samples of DNA are isolated from each patient. One DNA sample is isolated from neoplastic tissue and a second sample is isolated from non-neoplastic tissue. The non-neoplastic tissue can be of the same type as the neoplastic tissue or from a different organ source. It is desirable that the neoplastic tissue contains primarily neoplastic cells and that normal cells be separated from the neoplastic tissue. Ways for separating cancerous from non-cancerous cells are known in the art and any such means can be used. For example, DNA isolation from paraffin sections and cryostat sections can be used, as well as flow cytometry to separate aneuploid cells from diploid cells. DNA can also be isolated from tissues preserved in plastic. Separations based on cell size or density may also be used. Once the tissues have been isolated, DNA can be isolated from the tissue using any means known in the art. The tissue can be minced or homogenized and then the resulting cells can be lysed using a mixture of enzyme and detergent as described in Maniatis, *Molecular Cloning, a laboratory manual*, Cold Spring Harbor Laboratory, 1982. The nucleic acids can be extracted using standard techniques such as phenol and chloroform extraction, and ethanol precipitation.

Testing for the loss of a particular allele can be accomplished by a number of means which are described below. As alluded to above, it is desirable that the alleles used in the allelotype loss analysis be those for which the patient is heterozygous. This can be determined by examining the second sample of DNA which is isolated from non-neoplastic tissue of the patient and noting the size and number of fragments which hybridize to a particular nucleic acid probe for an allele for which there is restriction fragment length polymorphism. For example, where a homozygote would have only a single fragment generated by a particular restriction enzyme which hybridizes to a restriction fragment length polymorphism probe, a heterozygote would have two distinctly sized fragments which hybridize to the same probe generated by the enzyme. Determination of heterozygosis is well within the skill of the art.

Loss of an allele is determined by comparing the pattern of fragments corresponding to the allele in the normal tissue to the neoplastic tissue. For example, if a neoplastic tissue has two fragments for a particular allele and the neoplastic tissue has one fragment, a loss or deletion is scored. The number of such allelic losses divided by the number of alleles for which the patient is heterozygous yields an indicator factor called FAL (fractional allelic loss) or percentage loss of alleles. The FAL has proven to be a significant factor in prognosis of cancer as shown below in Table 3. The FAL provides a predictive index of metastasis, tumor recurrence, and resulting death.

One means of testing for loss of an allele is by digesting the first and second DNA samples of the neoplastic and non-neoplastic tissues, respectively, with a restriction endonuclease. Restriction endonucleases are well known in the art. Because they cleave DNA at specific sequences, they can be used to form a discrete set of DNA fragments from each DNA sample. The restriction fragments of each DNA sample can be separated by any means known in the art. For example, an electrophoretic gel matrix can be employed, such as agarose or polyacrylamide, to electrophoretically separate fragments according to physical properties such as size. The restriction fragments can be hybridized to nucleic acid probes which detect restriction fragment length polymorphisms, as described above. Upon hybridization hybrid duplexes are formed which comprise at least a single strand of probe and a single strand of the corresponding restriction fragment. Various hybridization techniques are known in the art, including both liquid and solid phase techniques. One particularly useful method employs transferring the separated fragments from an electrophoretic gel matrix to a solid support such as nylon or filter paper so that the fragments retain the relative orientation which they had on the electrophoretic gel matrix. The hybrid duplexes can be detected by any means known in the art, for example, the hybrid duplexes can be detected by autoradiography if the nucleic acid probes have been radioactively labeled. Other labeling and detection means are known in the art and may be used in the practice of the present invention.

An alternative means for testing for the presence of allelic deletions is by using the technique known in the art as PCR (polymerase chain reaction). According to this method discrete regions of DNA containing restriction fragment length polymorphisms are amplified. Amplification is accomplished by annealing, i.e., hybridizing a pair of single stranded primers, usually comprising DNA, to the DNA of said first and second samples from a patient. The primers are annealed to opposite strands of the DNA so that they prime DNA synthesis in opposite but convergent directions on a chromosome. The pair of primers bracket a region of DNA which contains a restriction fragment length polymorphism. That is to say that the primers anneal to DNA which is adjacent to the restriction fragment length polymorphism. Amplification of the region containing the restriction fragment length polymorphism is accomplished by repeated cycles of DNA synthesis catalyzed by a DNA polymerase. Preferably the DNA polymerase is Taq polymerase which is relatively heat insensitive. The DNA synthesis requires the components for DNA synthesis, i.e., each of the four deoxyribonucleotide triphosphates. In order to start a new cycle of DNA synthesis the primers must be separated from the DNA templates, i.e., the DNA of the first and second samples; the separation is readily accomplished by heating to above the melting point for duplex DNA. To restart the next cycle of synthesis the primers and template DNA are re-annealed. After approximately ten cycles it is desirable to add additional DNA polymerase to the reaction mixture. The product of the amplification is a duplex DNA fragment, bounded by the primers. The PCR technique is described in U.S. Pat. Nos. 4,683,195; 4,683,202; and 4,683,194, which are incorporated by reference herein.

The amplified region of DNA bracketed by the pair of primers can be detected in a number of ways. For example, the amplified DNA samples can be separated on an electrophoretic gel matrix and the separated DNA can be stained with ethidium bromide. These techniques are very well known in the art. In some cases, cleavage of the amplified DNA samples with a restriction endonuclease which recognizes a polymorphic sequence within the amplified region of DNA is required to generate polymorphic fragments. The amplified DNA can be separated on an electrophoretic gel matrix and subsequently transferred to a solid support (such as nylon or paper) on which hybridization with a nucleic acid probe can occur. The nucleic acid probe is one which is homologous with either one of the pair of primers or with the bracketed region of DNA. The nucleic acid probe can be detected by any means known in the art. Commonly, radioactivity will be used to label the probe and detection will be by autoradiography.

Primers for use in the polymerase chain reaction technique can be designed using the probes which detect restriction fragment length polymorphisms. The primers may be ends of the DNA probes or other portions which when used still are able to bracket the region containing the RFLP allele. Primers can be tested for their usefulness using DNA which is known to contain a restriction fragment length polymorphism. For example, a DNA sample from a normal tissue of a patient which has been shown by a probe to be heterozygous for a particular allele can be used to test out a pair of primers. If the pair of primers, upon amplification of the DNA sample, yields two or more fragments, then the primers are useful in the method of the present invention.

Kits are also provided by the present invention which contain either sets of nucleic acid probes or sets of primer pairs or both. The kits contain sufficient numbers of probes or primers such that the cumulative loss of a large enough number of alleles can be determined to provide a measure of extent of change in neoplastic tissues. The measure is correlated with prognosis. The nucleic acids in said kits may be provided in solution or lyophilized form. Preferably, the nucleic acids will be sterile and devoid of nucleases to maximize shelf-life.

The following examples are not intended to limit the scope of the invention. They are provided merely to teach concrete and practical means for carrying out the invention.

EXAMPLE 1

This example demonstrates a way in which allelic deletion analysis can be performed.

Figure 3A:
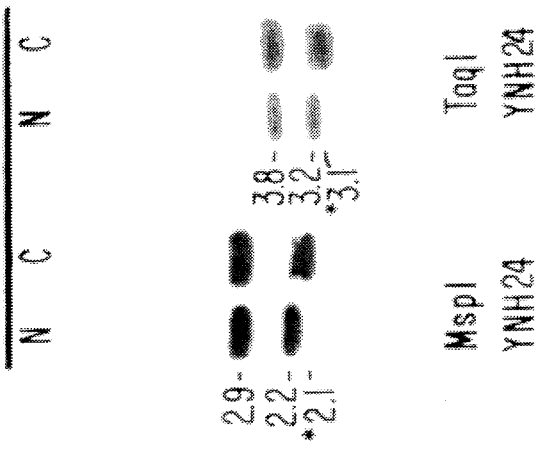

DNA from normal (N) and carcinoma (C) tissues of patient S141 (tumor A) was cleaved with restriction endonucleases (TaqI and MspI) and the fragments were separated by electrophoresis and transferred to nylon filters. The filters were incubated with the indicated radioactive probes. Results are shown in FIG. 3A. Sizes of the polymorphic restriction fragments are shown on the left of each fragment. With probes RM7.4 and g3, the larger allele was lost from the tumor; with probe EFD 64.1, the smaller allele was lost. The sources and descriptions of the probes are listed below in Example 2.

EXAMPLE 2

This example demonstrates the allelotypic analysis of 56 primary colorectal carcinomas, and the amount of allelic loss in the tumor population for each chromosomal arm.

DNA was purified from cryostat sections of 56 primary colorectal carcinomas removed at surgery and compared to the DNA from normal colonic tissue of the same patients. Probes detecting RFLPs were used to determine whether one of the two parental alleles detected by each probe was specifically lost in the DNA from the tumor cells. All non-acrocentric autosomal arms were studied; the only genes known to be present on the acrocentric arms (13p, 14p, 15p, 21p, and 22p) are ribosomal. For each of the 39 non-acrocentric chromosomal arms, enough probes were used to ensure that the two parental alleles could be distinguished in the normal tissue of at least 20 patients (i.e., the informative patients).

The probes used to study the allelotypic deletions are listed below:

Chromosome 1p (36 informative tumors)—Probe YNZ 2: Y. Nakamura et al., Nucleic Acids Res. 16, 4747 (1988); Chromosome 1q (47 informative tumors)—Probe YNA 13; Y. Nakamura and R. White, Nucleic Acids Res. 16, 9369 (1988); Chromosome 2p (27 informative tumors)—Probe EFD 122: E. Fujimoro et al., Nucleic Acids Res. 15, 10078 (1987); Chromosome 2q (45 informative tumors)—Probe YNH 24: Y. Nakamura et al., Nucleic Acids Res. 15, 10073 (1987); Chromosome 3p (25 informative tumors)—Probe EFD 145: E. Fujimoto et al., Nucleic Acids Res. 16, 9357 (1988); Chromosome 3q (26 informative tumors)—Probe EFD 64.1: Y. Nakamura et al., Nucleic Acids Res. in press; Chromosome 4p (23 informative tumors)—Probe YNZ 32: Y. Nakamura et al., Nucleic Acids Res. 16, 4186 (1988); Chromosome 4q (20 informative tumors)—Probe KT 218: S Humphries et al., Hum Genet 68, 148 (1984); Chromosome 5p (31 informative tumors) Probes JON 35 E–A and J0209 E–B: J. Overhauser, J. McMahan and J. Wasmuth, Nucleic Acids Res. 15, 4617 (1987); Chromosome 5q (55 informative tumors)—Probes 213–205, TP5E, C11P11, HF12–65, 105–153; M. Leppert et al., Science 238, 1411 (1987); Chromosome 6p (32 informative tumors)—Probe YNZ 132: Y. Nakamura et al., Nucleic Acids Res. 16, 5708 (1988); Chromosome 6q (31 informative tumors)—Probe Chromosome 7p (22 informative tumors)—Probe RM 7.4: R. Myers, et al., Nucleic Acids Res. 16, 3591 (1988); Chromosome 7q (51 informative tumors)—Probe g3: Z. Wong, V. Wilson, A. J. Jeffreys, S. L. Thein, Nucleic Acids Res. 14, 4605 (1988); Chromosome 8p (22 informative tumors)—Probe NF-L: G. Lacoste-Royal, M. Mathieu, J. P. Julfen, S. Gauthier, and D. Gauvreau, Nucleic Acids Res. 16, 4184 (1988); Probe SW 50: S. Wood et al., Cytogenet. Cell Genet. 42, 113 (1986); Chromosome 8q (26 informative tumors)—Probe MCT 128.2: Y. Nakamura et al., Nucleic Acids Res. 16, 3590 (1988); Chromosome 9p (27 informative tumors)—Probe MCT 112: M. Carlson et al., Nucleic Acids Res. 15, 10614 (1987); Probe HHH 220: M. Hoff et al., Nucleic Acids Res. 15, 10606 (1987); Chromosome 9q (39 informative tumors)—Probe EFD 126.3: Y. Nakamura et al., Nucleic Acids Res. 15, 10607 (1987); Chromosome 10p (37 informative tumors)—Probe TBQ 7: T. Bragg, Y. Nakamura, C. Jones and R. White, Nucleic Acids Res. in press (1989); Chromosome 10q (37 informative tumors)—Probe EFD 75: Y. Nakamura, E. Fujimoro and R. White, Nucleic Acids Res. in press (1989); Chromosome 11p (33 informative tumors)—Probe EJ: C. Shih and R.A. Weinberg, Cell 29, 161 (1982); Chromosome 11q (28 informative tumors)— Probe MCT 128.1: M. Carlson et al., Nucleic Acids Res. 16, 378 (1988); Chromosome 12p (39 informative tumors)— Probe EFD 33.2: E. Fujimoro, R. Myers, Y. Nakamura, R. White, Nucleic Acids Res. submitted (1988); Chromosome 12q (24 informative tumors) Probe YNH 15: Y. Nakamura et al., Nucleic Acids Res. 16, 770 (1988); Chromosome 13q (44 informative tumors)—Probe MHZ 47: Y. Nakamura et al., Nucleic Acids Res. 16, 3119 (1988); Chromosome 14q (50 informative tumors)—Probe CMM 101: Y. Nakamura et al., Nucleic Acids Res. 16, 381 (1988); Chromosome 15q (24 informative tumors)—Probe THH 55: T. Holm et al., Nucleic Acids Res. 16, 3117 (1988); Chromosome 16p (27 informative tumors)—Probe EKDMA2: E. Wolff et al., Nucleic Acids Res. 16, 9885 (1988); Chromosome 16q (42 informative tumors)—Probe 79-2-23: L. Burton et al., Hum. Genet. 74, 425 (1986); Chromosome 17p (56 informative tumors)—Probe YNZ 22: Y. Nakamura et al., Nucleic Acids Res. 16, 5707 (1988); Probe YNH 37.3: Y. Nakamura et al., Nucleic Acids Res. 16, 782 (1988); Probe MCT 35.1: M. Carlson et al. Nucleic Acids Res. 16, 700 (1988); Chromosome 17q (44 informative tumors)—Probe Htk9: Murphy, P.D. et al., Nucleic Acids Res. 14, 4381 (1986); Probe THH 59: Y. Nakamura et al., Nucleic Acids Res. 16, 3598 (1988); Chromosome 18p (27 informative tumors)—Probe B74: F. Morle et al., Cytogenet. Cell Genet. 37 544 (1984); Chromosome 18q (53 informative tumors)— Probe OS-4: Nishisho, I. et al., Jpn. J. Hum. Genet 32, 1 (1987); Probe OLVIIA8: Delattre, O. et al., Nucleic Acids Res. 15, 1343 (1987); Probe OLVII E10: Marlhens, F., et al., Nucleic Acids Res. 15, 1348 (1987); Probe HHH64: Yoshioka K., Yoshioka, N. Nakabepu, K., Sakaki, Y., Nucleic Acids Res. 14, 3147 (1986); Probe ERT 25: Muller, U. et al., Cytogenet. Cell Genet 46, 16 (1987); Chromosome 19p (44 informative tumors)—Probe JCZ 3.1: Y. Nakamura et al., Nucleic Acids Res. 16, 1229 (1988); Chromosome 19q (37 informative tumors)—Probe RB1–4: C. Julier, E. Wolff, Y. Nakamura, and R. White, Nucleic Acids Res. in press (1989); Chromosome 20p (46 informative tumors)—Probe CMM6: Y. Nakamura et al., Nucleic Acids Res. 16, 5222 (1988); Chromosome 20q (22 informative tumors)—Probe MS1–27: D. Barker, M. Schafer and R. White, Cell 36, 131 (1984); Chromosome 21q (27 informative tumors)—Probe MCT 15: Y. Nakamura et al., Nucleic Acids Res. 16, 9882 (1988); Chromosome 22q (41 informative tumors)—Probe EFZ 31: K. Krapcho et al. Nucleic Acids Res. 16, 5221 (1988); Probe AEB2.3: C.M. Rubin et al., Nucleic Acids Res. in pres (1989); Probe EW7.2: T. Bragg, Y. Nakamura, E. Wolff, J.-M. Lalouel and R. White, Nucleic Acids Res. in press (1989).

Allelic deletions were evaluated with restriction fragment length polymorphism analyses, examples of which are shown in FIG. 3. DNA from paired normal colonic mucosa and tumor tissues were cleaved with one of three enzymes (Taq I, Msp I, or HindIII), and evaluated with probes from each non-acrocentric chromosomal arm. Only informative tumors, i.e., those in which DNA from the normal tissue exhibited a heterozygous pattern for one or more allelic markers from the indicated chromosomal arm, were used to determine allelic loss frequencies. An allelic loss was scored if an RFLP fragment present in normal DNA was lost in at least 80% of the neoplastic cells, as assessed by comparison of the autoradiographs with histologic evaluation of the cryostat sections from which the tumor DNA was purified.

Alleles from each chromosomal arm were lost in at least some tumors (See FIG. 1 and Table I). The frequency of allelic loss varied considerably, however, with alleles from two chromosomal arms (17p and 18q) lost from over 75% of tumors, alleles from nine arms 5q, 6p, 6q, 8p, 9q, 18p, 22q) lost in 25 to 50% of tumors, and alleles from the remaining 28 arms lost in 7–24% of the tumors.

TABLE I

LOSS OF ALLELES FROM AUTOSOMAL ARMS

| CHROMOSOME | MARKER[a] | MARKER TYPE[b] | ENZYME[c] | # INFORMATIVE TUMORS[d] | % OF TUMORS WITH ALLELIC LOSS[e] |
|---|---|---|---|---|---|
| 1p | YNZ2 | V | T | 36 | 16.2% |
| 1q | YNA13 | V | T | 47 | 25.5% |
| 2p | EFD122 | S | M | 27 | 7.4% |
| 2q | YNH24 | V | M | 45 | 8.9% |
| 3p | EFD 145 | S | T | 25 | 20.0% |
| 3q | EFD 64.1 | V | T | 26 | 15.4% |
| 4p | YNZ 32 | V | T | 23 | 26.1% |
| 4q | KT 218; TBZ 34 | S;S | T;M | 20 | 10.0% |
| 5p | JON35E-A; JO209E-B | S;S | M;M | 31 | 6.5% |
| 5q | 213–205; TP5E; C11P11; HF12-65; 105–153 | S;S; S;S; S | M;T;T; M;M | 55 | 36.4% |
| 6p | YNZ 132 | V | T | 32 | 25.0% |
| 6q | JCZ 30 | V | H | 31 | 32.3% |
| 7p | RM 7.4 | S | M | 22 | 9.1% |
| 7q | g3 | V | T | 51 | 11.8% |
| 8p | NF-L; SW 50 | S;S | T;H | 22 | 50.0% |
| 8q | MCT 128.2 | V | T | 26 | 7.7% |
| 9p | MCT 112; HHH 220 | S;S | M;T | 27 | 22.2% |
| 9q | EFD 126.3 | V | M | 39 | 25.6% |
| 10p | TBQ 7 | V | M | 37 | 8.1% |
| 10q | EFD 75 | V | T | 37 | 13.5% |
| 11p | EJ | V | T | 33 | 15.2% |
| 11q | MCT 128.1 | S | M | 28 | 14.3% |
| 12p | EFD 33.2 | S | M | 39 | 7.7% |
| 12q | YNH 15 | S | M | 24 | 16.7% |
| 13q | MHZ 47 | V | T | 44 | 11.4% |
| 14q | CMM 101 | V | M | 50 | 20.0% |
| 15q | THH 55 | S | M | 24 | 12.5% |
| 16p | EKA2 | V | M | 27 | 7.4% |
| 16q | 79-2-23 | V | T | 42 | 11.9% |
| 17p | YNZ 22; YNH 37.3; MCT 35 | V;V; V | T;T;M | 56 | 80.4% |
| 17q | Htk9; THH 59 | S;V | T;T | 44 | 15.9% |
| 18p | B74 | S | T | 27 | 44.4% |
| 18q | OS-4; OL VII AB OL VII E10; HHH64; ERT 25 | S;S S;S V | T;M; M;M; T | 53 | 77.4% |
| 19p | JCZ 3.1 | V | T | 44 | 11.4% |
| 19q | RB1–4 | V | T | 37 | 16.2% |
| 20p | CMM6 | V | T | 46 | 8.7% |
| 20q | MS1-27 | S | M | 22 | 9.1% |
| 21q | MCT 15 | V | M | 27 | 22.2% |
| 22q | EFZ31; A-EB2.3; EW7.2 | S;S;V | M;T;M | 41 | 29.3% |

[a]References to the markers are given in EXAMPLE 2
[b]"V" signifies VNTR markers; "S" signifies restriction site polymorphism markers.
[c]M = MspI; T = Taq I; H = HindIII
[d]# of tumors in which one or more markers for the indicated chromosomal arm were informative (i.e., DNA from corresponding normal tissue exhibited a heterozygous pattern).
[e]Only informative tumors were used to assess this percentage. Losses were scored positively only if they were clonal, as described in the text.

There were 127 examples of allelic deletions in which the patient was informative (heterozygous) for markers on both the p and q arms of the chromosome containing the deletion. In 65% of these cases, allelic loss occurred in only one of the two chromosomal arms. The majority of the deletions observed in this study therefore represented sub-chromosomal events, such as might be mediated by interstitial deletion, mitotic recombination, or gene conversion, rather than loss of a whole chromosome.

EXAMPLE 3

This example demonstrates the amount of allelic loss for individual tumors.

Figure 2:
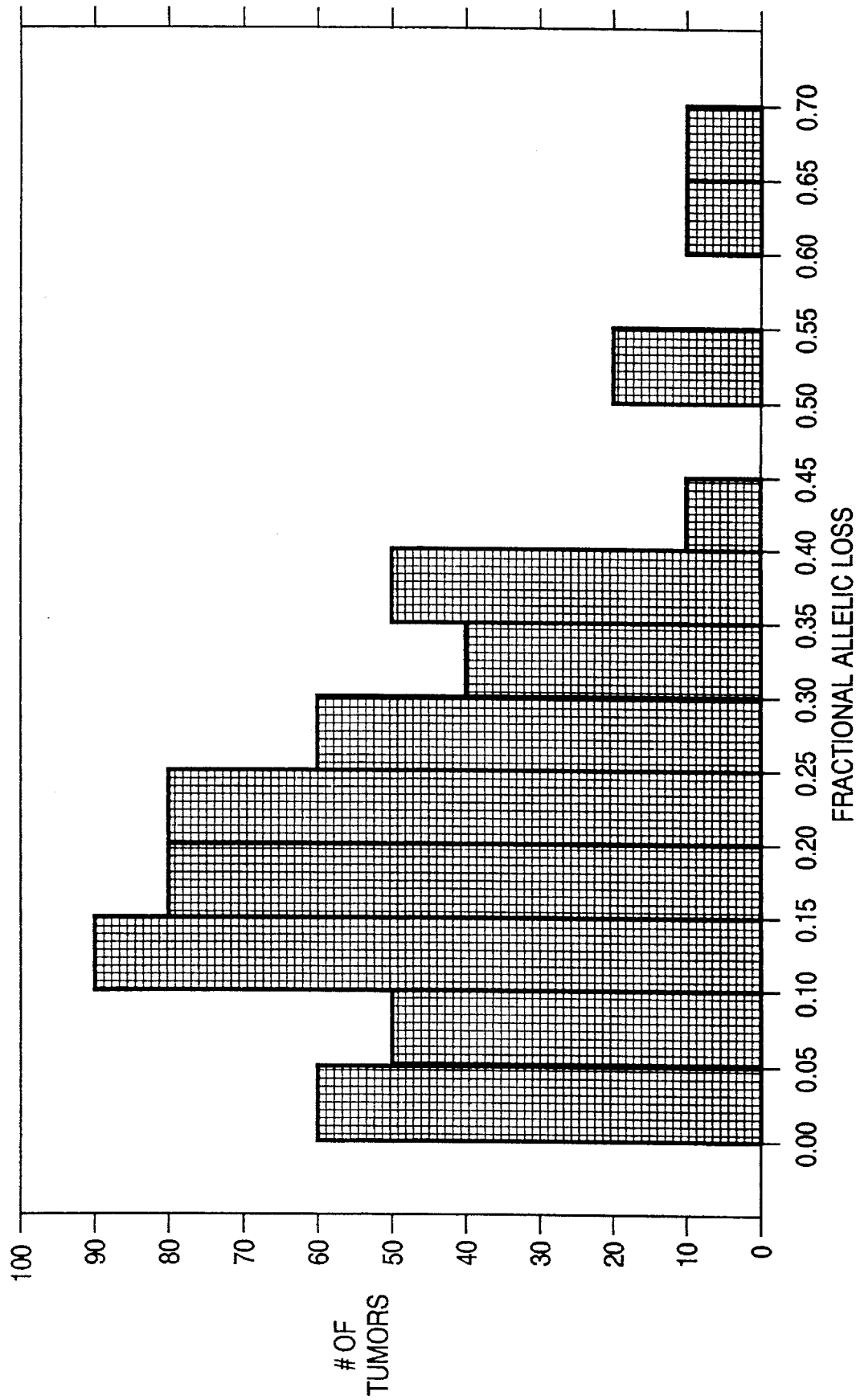
FIG. 2 shows the accumulated allelic losses in individual tumors. The fractional allelic loss in each tumor is defined as the number of chromosomal arms on which the allelic loss was observed divided by the number of chromosomal arms for which allelic markers were informative (i.e., those in which DNA from the normal tissue exhibited a heterozygous pattern).

We defined fractional allelic loss (FAL) in a tumor as the number of chromosomal arms on which allelic loss was observed divided by the number of chromosome arms for which allelic markers were informative (heterozygous) in the patient's normal cells. The median FAL in the 56 tumors studied was 0.20, in other words, alleles were lost from 20% of the evaluable chromosomal arms. In 12 tumors, more than a third of the evaluable chromosomal arms had undergone allelic deletion. (See FIG. 2 and Table II)

TABLE II

LOSS OF ALLELES IN INDIVIDUAL TUMORS

| TUMOR[a] | CHROMOSOMAL ARMS ON WHICH ALLELIC MARKERS WERE LOST | # OF ARMS WITH NO LOSS[b] | FAL[c] |
|---|---|---|---|
| S7 | 7q,18q,20p | 19 | 13.6 |
| S15 | 5q,17p,18q | 17 | 15.0 |
| S16 | 17p,18q | 19 | 9.5 |
| S20 | 9q,12q,17p,18q,20q,22q | 17 | 26.1 |
| S22 | 1p,8p,17p,18p,18q | 25 | 16.7 |
| S43 | 1p,1q,3q,4p,5q,11p,13q,14q,17p,18q | 5 | 66.7 |
| S45 | 10q,15p,17p,18p,18q | 24 | 17.2 |
| S50 | 2p,2q,6p,6q,8p,15q,17p,17q,18q,21q | 20 | 33.3 |
| S51 | 4p,14q,17p,18q | 20 | 16.6 |
| S59 | 1q,4p,5q,13q,17p,18p,18q,19p,19q | 15 | 37.5 |
| S61 | 9q,17p,18q | 17 | 15.0 |
| S62 | 17p,21q | 22 | 8.3 |
| S67 | 1p,5p,5q,11q,17p,18q | 23 | 20.7 |
| S74 | 4p,5q,7q,11p,12q,16p,16q,17p,18q,19q,22q | 10 | 52.4 |
| S82 | 5q | 22 | 4.3 |
| S89 | 1q | 24 | 4.0 |
| S91 | 1p,5q,10q,12p,16q,17p,22q | 18 | 28.0 |
| S92 | | 20 | 0.0 |
| S93 | 1q,5q,6p,6q,10p,15q,17p,17q | 19 | 29.6 |
| S96 | 5q,9p,16q,17p,22q | 21 | 19.2 |
| S98 | 2q,9q,15q,17p | 21 | 16.0 |
| S99 | 13q,17p,18q | 18 | 14.3 |
| S103 | 14q,17p,18q | 20 | 13.0 |
| S104 | | 24 | 0.0 |
| S106 | 4p,5q,8p,9p,17p,17q,18p,18q | 14 | 36.4 |
| S108 | 10q,17p,18q,19q | 21 | 16.0 |
| S109 | 6p,6q,16q,17p,19p | 17 | 22.7 |
| S115 | 5q,14q,17p,17q,18q,21q | 18 | 25.0 |
| S119-A | 1q,6p,6q,14q,17p,18p,18q,21q | 14 | 39.1 |
| S119-D | 6q,9q,18q | 20 | 13.0 |
| S122 | 3p,6p,6q,8p,9p,9q,17p,17q,18q,22q | 19 | 34.5 |
| S123 | 1q,5q,6p,6q,7p,7q,9q,18q | 18 | 30.8 |
| S124 | 1q,2q,3q,4q,6p,6q,7q,9q,11p,14q,17p,18q,19q | 11 | 54.2 |
| S126 | 3q | 22 | 4.3 |
| S133 | 3p,5p,5q,6p,6q,11p,17p,17q,20p | 16 | 36.0 |
| S136 | 1q,3p,16q,17p,18q,19p | 23 | 20.7 |
| S140 | 4q,5q,8p,12q,17p,18q,19q | 18 | 28.0 |
| S141-A | 3q,7p,7q,8p,10p,10q,13q,14q,17p,17q,18p,18q,19p,19q,22q | 9 | 62.5 |
| S141-B | 8p,9p,10p,11q,14q,17p,18p,18q,22q | 15 | 37.5 |
| S153 | 1q,7q,8p,17p,18q,22q | 20 | 23.1 |
| S154 | 4p,17p,18q | 21 | 12.5 |
| S161 | 1p,1q,5q,8p,8q,17p,18q,20p,20q | 20 | 31.0 |
| S162 | 1q,5q,6q,8p,8q,10q,12p,17p,18q,21q,22q | 14 | 44.0 |
| S165 | 5q,9p,9q,13q,17p | 16 | 23.8 |
| S167 | 3p,9q,14q,17p,18p,18q,21q,22q | 21 | 27.6 |
| S168 | 1q,5q,17p,18q | 22 | 15.4 |
| S170 | 5q,18q,22q | 27 | 10.0 |
| S173 | | 21 | 0.0 |
| S174 | 8p,11p,11q,14q,17p,18p,18q | 21 | 25.0 |
| S175 | 18q,20p | 27 | 6.9 |
| S177 | 17p,18p,18q | 17 | 15.0 |
| S184 | 17p,18q | 22 | 8.3 |
| S190 | 1p,3p,9p,9q,12q,17p,18p,18q | 19 | 29.6 |
| S191 | 2q,5q,17p,19p | 21 | 16.0 |
| PS-6 | 2p,11q,12p,17p,18q | 17 | 22.7 |
| PS-12 | 17p,18p,18q | 21 | 12.5 |

[a] Two patients (S119 and S141) had two separate tumors.
[b] = # of arms on which DNA from normal tissue demonstrated heterozygosity with one or more allelic markers, but both alleles were retained in tumor DNA.
[c] = Fractional Allelic Loss, as defined in the text.

EXAMPLE 4

This example demonstrates the prognostic value of Fractional Allelic Loss.

The patients were divided into two groups: those with tumors containing less than the median FAL (Group I, FAL less than 0.2) and those containing greater than the median (Group II). Both groups of patients were followed for a period averaging 38 months. The two groups of patients were of similar sex distribution and age, and the average size and extent of invasion (Dukes' classification) of their tumors were nearly identical. The prevalence of another genetic alteration (Ras. gene mutation) that occurs commonly in colorectal tumors was identical in the two groups. Despite these similarities, the patients with more deletions (higher FAL) were significantly more likely to develop recurrent disease than the other group (p less than 0.01). See Table III. These patients were also significantly more likely to die with or from their cancer (p less than 0.01).

TABLE III

| GROUP[a] | FRACTIONAL ALLELIC LOSS (MEAN) | # OF PATIENTS[b] | AGE (MEAN) | FOLLOW-UP PERIOD (MEAN)[c] | TUMOR SIZE (MEAN) | DUKES' CLASS (MEAN)[d] | RAS MUTATION[e] | TUMOR RECURRENCE[f] | DEATH[g] |
|---|---|---|---|---|---|---|---|---|---|
| I | 0.11 | 27 | 67 YEARS | 38 MTHS | 5.3 cm | 2.3 | 52% | 30% | 26% |
| II | 0.32 | 25 | 67 YEARS | 38 MTHS | 5.6 cm | 2.4 | 52% | 68% | 64% |
| P VALUE | | | NS | NS | NS | NS | NS | <0.01 | <0.01 |

[a] Group I patients had tumors with a Fractional Allelic Loss (FAL) less than the median value (0.2) of the 56 tumors listed in Table 2; Group II patients had tumors with an FAL greater than 0.2.
[b] All patients from Table II with a single carcinoma were included.
[c] Average follow-up period in patients who survive is listed. The average follow-up period in all patients combined (i.e., those who are still alive plus those who died) was 31 and 17.5 mths for group I and II patients, respectively.
[d] Dukes' classification scored as 1.0 for Dukes' A tumors (confined to muscularis propria); 2.0 for Dukes' B tumors (extension through muscularis propria); and 3.0 for Dukes' C tumors (metastatic to regional lymph nodes)
[e] RAS gene mutations in this group of tumors were reported previously.
[f] Distant metastases developed in all except one patient who developed tumor recurrence.
[g] Death with or from carcinoma. An additional 6% and 12% of group I and II patients, respectively, died without definite evidence of recurrent carcinoma.

TABLE III-continued

| GROUP[a] | FRACTIONAL ALLELIC LOSS (MEAN) | # OF PATIENTS[b] | AGE (MEAN) | FOLLOW-UP PERIOD (MEAN)[c] | TUMOR SIZE (MEAN) | DUKES' CLASS (MEAN)[d] | RAS MUTATION[e] | TUMOR RECURRENCE[f] | DEATH[g] |
|---|---|---|---|---|---|---|---|---|---|

[h]Student's T test.
[i]Fisher's exact test.

There was also a significant relationship between allelic deletions and clinical course in the subset of patients with leas advanced disease at the time of surgery (Dukes' stage A or B). In 14 such patients with more than the median FAL, 11 (79%) developed recurrent disease (usually distant metastases) post-operatively. Only two of fourteen stage A or B patients in the low FAL group had tumor recurrence (p less than 0.001, Fisher's exact test). Thus the measurement of allelic losses might help to identify patients with an otherwise relatively favorable prognosis who could benefit from additional therapy.

EXAMPLE 5

This example demonstrates that genetic variations other than deletions occur in cancer patients and are detectable by the method of the present invention.

In five different instances of allelotype analysis as described above in Example 1, new bands not observed in the DNA from normal tissue were found in DNA from the corresponding tumor. Each case involved a probe from a different chromosomal arm, and these five probes were all of the VNTR type (See FIG. 3B–F).

Figure 3B:
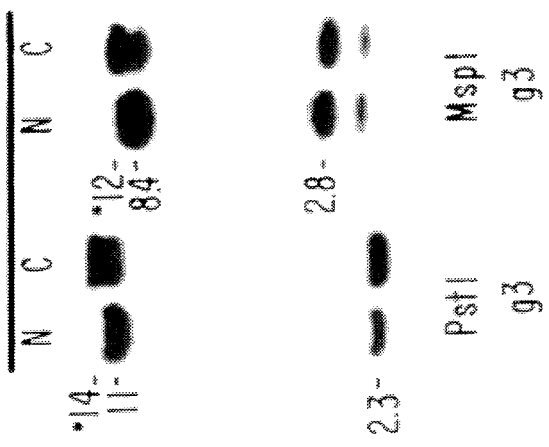
Figure 3C:
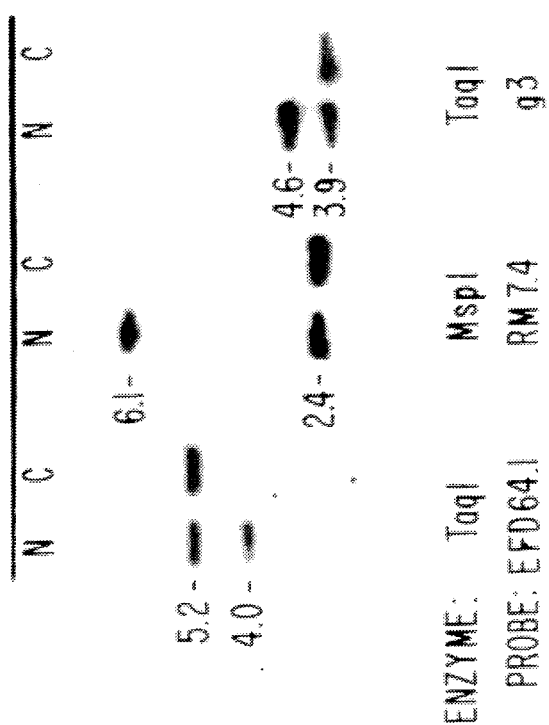

Autoradiographs of Southern blots prepared as described in FIG. 3, panel A, are shown in FIG. 3B–F. For each normal (N)-carcinoma (C) pair, the results of digestion with two different enzymes are shown, and the probe is indicated. B: Patient S7; C: Patient S191; D: Patient S153; E: Patient S98; F: Patient S175. Sizes of the major polymorphic restriction fragments are shown on the left of each autoradiograph, and the new fragments in the tumor samples are marked with asterisks.

Areas of tumors containing a high proportion of neoplastic cells were isolated and 12 micron thick cryostat sections of these areas were used to prepare DNA. Grossly normal colonic mucosae adjacent to the tumors were obtained from each patient and used to prepare control (normal) DNA. DNA purification, restriction endonuclease digestion, electrophoresis, Southern transfer, and DNA hybridization were performed as described (Nature, 318; 377 (1985) and Cancer Research, 47; 4806 (1987)).

The size of the new bands in an individual tumor was either decreased (in tumors number S98, S153, and S191) or increased (in tumors S7 and S175) by a similar number of base pairs regardless of the enzyme used). Although the occurrence of VNTR changes in DNA fragments containing VNTR sequences was rare (five alleles altered of 2900 VNTR alleles examined), no rearrangements of fragments without VNTR sequences were observed in our study (3100 alleles were examined with non-VNTR probes).

I claim:

1. A method of selecting a set of alleles for use in cancer prognosis, comprising the steps of:

hybridizing a set of probes or primers able to hybridize to alleles on different human chromosome arms to DNA isolated from cancerous and noncancerous cells of a population of patients with cancer to detect the presence or absence of the alleles;

determining a cumulative percent loss of alleles detected by the set of probes or primers in cancerous as compared to noncancerous cells for each patient;

following each patient of the population to ascertain a clinical outcome of said patient, said clinical outcome selected from the group consisting of recurrence of the cancer, metastasis, and death due to the cancer;

performing a statistical analysis to determine whether a correlation exists between the cumulative percent loss and the clinical outcome, the set of alleles being useful for cancer prognosis if said correlation exists.

2. A method for assessing fractional allelic loss in nucleic acids of cancerous cells as compared to noncancerous cells of an individual human patient having cancer, which fractional allelic loss is prognostic of clinical outcome of said individual patient, comprising the steps of:

(1) hybridizing a selected set of nucleic acid probes to nucleic acids isolated from cancer cells of said individual patient, said nucleic acids having been digested with a restriction endonuclease, each member of said selected set of nucleic acid probes being able to hybridize to an allele of a set of alleles, for which set of alleles a statistical relationship has been predetermined, which statistical relationship correlates:

(a) losses in said set of alleles in nucleic acids of cancerous cells from patients having cancer with (b) clinical outcome of said patients;

(2) hybridizing the selected set of nucleic acid probes of step (1) to nucleic acids isolated from non-cancerous cells of said individual patient, said nucleic acids having been digested with a restriction endonuclease;

(3) based on differences in hybridization characteristics of said selected set of nucleic acid probes to the nucleic acids of step (1) compared to the nucleic acids of step (2), determining the number of allelic losses in the nucleic acids isolated from cancerous cells of said individual patent; and (4) determining a fractional allelic loss value by dividing the number of allelic losses determined in step (3) by the number of alleles in the set of alleles probed for which said individual patient is heterozygous.

3. The method of claim 2 in which the nucleic acid probes are DNA.

4. The method of claim 2 in which the nucleic acid probes hybridize to genomic DNA regions which contain restriction fragment length polymorphisms.

5. The method of claim 2 in which the nucleic acid probes hybridize to genomic DNA regions which contain variable number of tandem repeats.

6. The method of claim 2 in which the set of alleles comprises alleles on chromosomal arms selected from the group consisting of 1q, 4p, 5q, 6p, 6q, 8p, 9q, 17p, 18p, 18q and 22q.

7. The method of claim 2 in which the set of alleles comprises alleles on chromosomal arms 17p and 18q.

8. A method for determining a prognosis of an individual human patient having cancer, comprising the steps of:
(1) obtaining a fractional allelic loss value for cancerous cells of an individual patient according to the method of claim 2;
(2) applying to said fractional allelic loss value of said individual patient a predetermined statistical relationship, which statistical relationship correlates (a) fractional allelic loss values of cancerous cells of a population of patients having said cancer with (b) clinical outcome; and
(3) predicting the clinical outcome of said individual patient.

9. A method for assessing fractional allelic loss in nucleic acids of cancerous cells as compared to noncancerous cells of an individual human patient having cancer, which fractional allelic loss is prognostic of clinical outcome of said individual patient, comprising the steps of:
(1) amplifying regions of nucleic acids isolated from cancer cells of said individual patient, using a selected set of pairs of nucleic acid primers, each pair of nucleic acid primers being able to hybridize to nucleic acids which bracket an allele of a set of alleles, for which set of alleles a statistical relationship has been predetermined, which statistical relationship correlates:
(a) losses in said set of alleles in nucleic acids of cancerous cells from patients having cancer, with
(b) clinical outcome of said patients;
(2) amplifying regions of nucleic acids isolated from non-cancerous cells of said individual patient with the selected set of pairs of primers of step (1);
(3) based on differences in regions amplified from the nucleic acids of step (1) compared to regions amplified from the nucleic acids of step (2), determining the number of allelic losses in the nucleic acids isolated from cancerous cells of said individual patient; and
(4) determining fractional allelic loss by dividing the number of allelic losses determined in step (3) by the number of alleles for which said individual patient is heterozygous in the set of alleles amplified.

10. The method of claim 9 in which the nucleic acid primers are DNA.

11. The method of claim 9 in which the pairs of nucleic acid primers bracket regions of DNA containing restriction fragment length polymorphisms.

12. The method of claim 9 in which the pairs of nucleic acid primers bracket regions of DNA containing variable number of tandem repeats.

13. The method of claim 9 in which the set of alleles comprises alleles on chromosomal arms selected from the group consisting of 1q, 4p, 5q, 6p, 6q, 8p, 9q, 17p, 18p, 18q and 22q.

14. The method of claim 9 in which the set of alleles comprises alleles on chromosomal arms 17p and 18q.

15. A method for determining a prognosis of an individual human patient having cancer, comprising the steps of:
(1) obtaining a fractional allelic loss value for cancerous cells of an individual patient according to the method of claim 9;
(2) applying to said fractional allelic loss value of said individual patient a predetermined statistical relationship, which statistical relationship correlates (a) fractional allelic loss values of cancerous cells of a population of patients having said cancer with (b) clinical outcome; and
(3) predicting the clinical outcome of said individual patient.

16. A kit useful for cancer prognosis comprising:
a selected set of nucleic acid probes, each member of said selected set of nucleic acid probes annealing to an allele of a set of alleles, for which set of alleles a statistical relationship has been predetermined, which statistical relationship correlates:
(a) loss in said set of alleles in nucleic acids of cancerous cells from a population
of patients afflicted by a particular type of cancer with
(b) clinical outcome of said patients; and
means for correlating a fractional allelic loss value determined using said set of nucleic acid probes with prognosis of said patients.

17. The kit of claim 16 wherein said probes anneal to variable number of tandem repeat sequences.

18. The kit of claim 16 wherein said set of probes comprises probes which anneal to at least one allele from each of the non-acrocentric chromosomal arms of the human genome.

19. The kit of claim 16 wherein said set of probes comprises probes for alleles on chromosomal arms selected from the group consisting of 1q, 4p, 5q, 6p, 6q, 8p, 9q, 17p, 18p, 18q and 22q.

20. The kit of claim 16 wherein said set of probes comprises probes for alleles on chromosomal arms selected from the group consisting of 17p and 18q.

21. A kit useful for cancer prognosis, comprising:
a selected set of pairs of nucleic acid primers, each pair of nucleic acid primers annealing to DNA which brackets an allele of a set of alleles, for which set of alleles a statistical relationship has been predetermined, which statistical relationship correlates:
(a) loss in said set of alleles in nucleic acids of cancerous cells from patients afflicted by a particular type of cancer with
(b) clinical outcome of said patients; and
means for correlating a fractional allelic loss value determined using said set of primers with prognosis of said patients.

22. The kit of claim 21 wherein said primer pairs anneal to DNA which brackets variable number of tandem repeat sequences.

23. The kit of claim 21 wherein said set of primers comprises primers which anneal to DNA bracketing alleles from each of the non-acrocentric chromosomal arms of the human genome.

24. The kit of claim 21 wherein said set of primers comprises primers for alleles on chromosomal arms selected from the group consisting of 1q, 4p, 5q, 6p, 6q, 8p, 9q, 17p, 18p, 18q and 22q.

25. The kit of claim 21 wherein said set of primers comprises primers for alleles on chromosomal arms selected from the group consisting of 17p and 18q.

* * * * *